US007310992B2

(12) United States Patent
Swank et al.

(10) Patent No.: US 7,310,992 B2
(45) Date of Patent: Dec. 25, 2007

(54) DEVICE FOR CONTINUOUS REAL-TIME MONITORING OF AMBIENT AIR

(75) Inventors: Freeman Swank, Olathe, KS (US);
Christopher Tesluk, Kansas City, MO (US)

(73) Assignee: Sceptor Industries, Inc., Kansas City, MO (US)

( * ) Notice: Subject to any disclaimer, the term of this patent is extended or adjusted under 35 U.S.C. 154(b) by 152 days.

(21) Appl. No.: 11/236,266

(22) Filed: Sep. 27, 2005

(65) Prior Publication Data
US 2007/0256476 A1    Nov. 8, 2007

(51) Int. Cl.
*G01N 1/10*    (2006.01)
*B01D 47/02*   (2006.01)
(52) U.S. Cl. .............. 73/31.01; 73/31.02; 73/31.03; 73/863.21; 95/219; 96/181; 96/209; 96/316; 96/413; 436/177; 436/178; 436/181
(58) Field of Classification Search .......... 73/31.01, 73/31.02, 31.03, 863.12, 863.21; 95/219; 96/181, 209, 316, 413; 261/76, 79.2; 436/52, 436/174, 177, 181
See application file for complete search history.

(56) References Cited
U.S. PATENT DOCUMENTS 5,011,517 A * 4/1991 Cage et al. .................. 95/220

5,679,580 A * 10/1997 Ball et al. .................. 436/177
5,861,316 A * 1/1999 Cage et al. .................. 436/52
5,988,603 A * 11/1999 McCampbell et al. ........ 261/76

OTHER PUBLICATIONS

Sceptor Industries, Inc.—OMNI 3000—Proven Performance in a Lightweight Sampler, Jun. 2, 2005, pp. 1-3.*
Sceptor Industries, Inc. "Sceptor's Portable Aersol Collector Equips First Responders, Environmental Managers With Homeland Security-Level Performance", Apr. 27, 2005, pp. 1-2.*
T-Squared Technology, Inc. "New SpinCon OMNI—Announcement", Apr. 11, 2005, pp. 1-2.*

* cited by examiner

*Primary Examiner*—Daniel S. Larkin
(74) *Attorney, Agent, or Firm*—Shook, Hardy & Bacon, L.L.P.

(57) ABSTRACT

The present invention provides a device for continuous real-time monitoring of ambient air. The device includes a receptacle, a liquid supply, and a pressure balancing system. The receptacle includes a gas inlet slit located such that the gas inlet slit is covered by liquid within the receptacle during use. The pressure balancing portion of the present device includes communication between a point within the receptacle above the liquid level in the receptacle, as well as a liquid inlet portion at the lowermost end of the receptacle, and an air space above a liquid supply portion and the liquid supply portion itself, respectively.

20 Claims, 5 Drawing Sheets

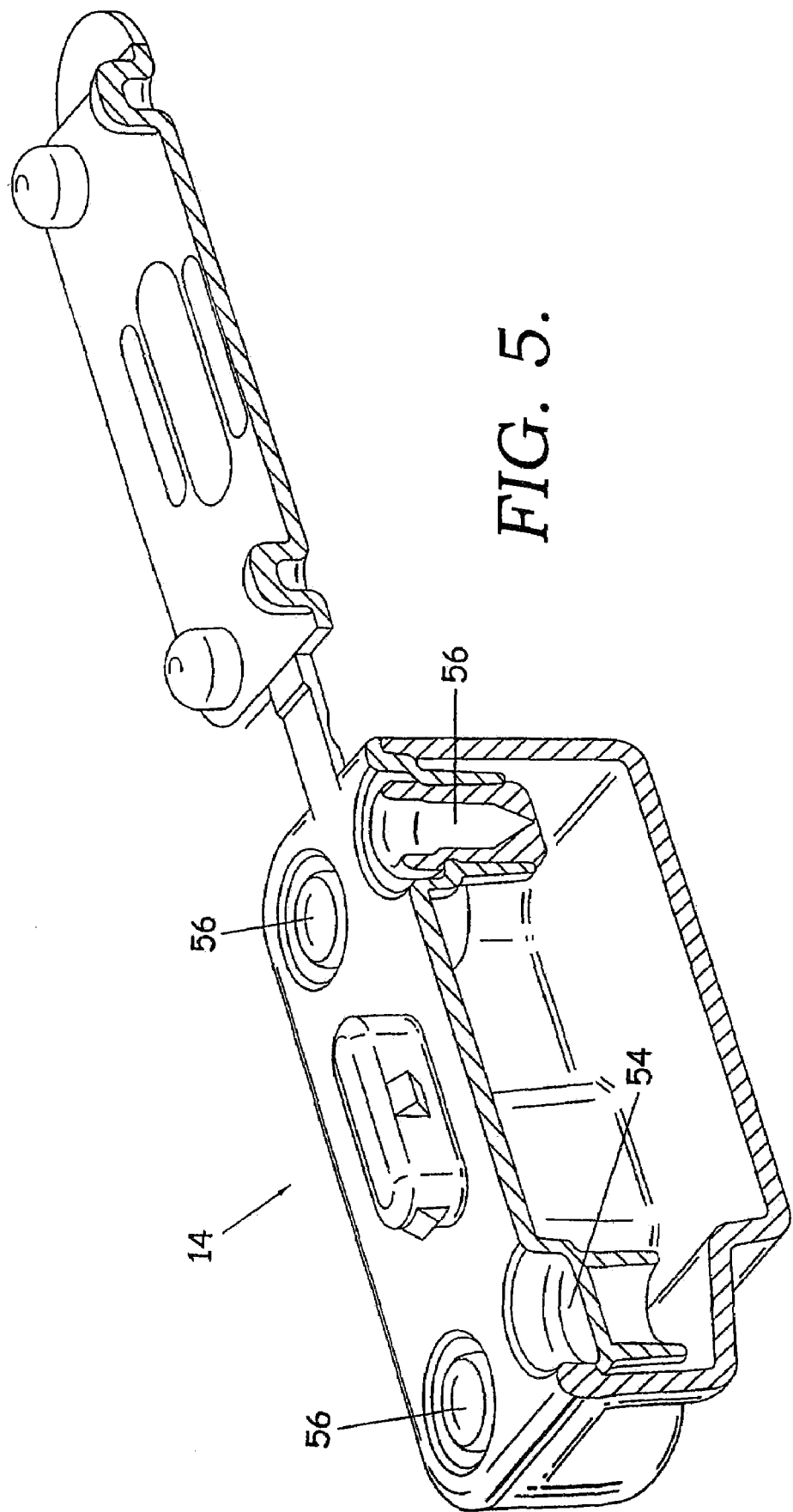

DEVICE FOR CONTINUOUS REAL-TIME MONITORING OF AMBIENT AIR

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

BACKGROUND OF THE INVENTION

The present invention relates generally to chemical and biological sampling, and more specifically to a system for real-time monitoring of ambient air for the presence of biological and chemical compounds.

The need for accurate, real-time systems for detection of chemical and biological compounds or agents in the ambient air has increased significantly in recent years. Such devices are useful in numerous areas, such as biological and chemical warfare monitoring and testing, and monitoring of environmental air conditions.

Since the end of the Cold War and the resulting decrease in tensions between international superpowers, regional stability between nationalistic, religious, and ethnic groups has risen, leading to substantial threats to peace across the globe. At the same time, advances in chemical and biological technology have lead to an increase in the availability of chemical and biological agents worldwide. Such agents are relatively inexpensive and easy to produce, making them attractive to various terrorist and other organizations. Since the events of Sep. 11, 2001, and the subsequent anthrax attacks, public and private awareness of the need to monitor the air for biological and chemical agents and compounds has increased.

In the case of biological and chemical warfare agents, it is often imperative (such as on a battlefield, for example) that a device for immediate, real-time sampling and analysis of the ambient air is available. Further, environmental air quality must, in some non-military situations, be sampled and analyzed in real-time. For example, measuring air quality in poorly-ventilated mines requires real-time collection and analysis of samples due to the immediate threat to the health and safety of persons in the mine posed by the presence of toxic gases or other compounds.

Prior art devices, such as that described in U.S. Pat. No. 5,861,316, provide the capability for real-time sampling and analysis of ambient air. Such devices, however, have certain deficiencies that are addressed by the present invention. The prior art device in the '316 patent, for example, includes a wet-wall contactor to collect airborne particles into a liquid. Maintaining the correct fluid level in such a collector is paramount to the success of the device. Optics-based systems can be rendered inadequate by bubbles, dirt, or contaminants in the liquid. Thus, there exists a need for an ambient air sampling device that provides improved fluid level control. In addition, the prior art devices typically include contactors having an inlet slit for passage of an air stream into the contactor, wherein the sampling fluid in the contactor covers approximately 40%-50% of the inlet slit. As a result, a substantial portion of the air stream is able to enter the contactor without passing through the fluid. What is needed, therefore, is a device wherein the entire inlet slit is covered by the contact fluid, such that all of the air stream entering the contactor passes into the fluid, requiring less power to effectively sample the same amount of air as the prior art device and resulting in a lighter, more easily portable device.

The present invention addresses the above and other limitations of the prior art.

BRIEF SUMMARY OF THE INVENTION

The present invention provides a device for continuous monitoring of ambient air or other gas. The device includes a receptacle with a generally cylindrical wall having a gas inlet slit therein. The slit is off-tangential to the wall of the receptacle. The receptacle further has instability points at or about the maximum and minimum levels of liquid that can be maintained in the receptacle during use. The device further includes a liquid supply portion to provide liquid to the receptacle, and a pressure balancing portion to maintain a level of liquid in the cylinder. The gas inlet slit in the receptacle is located such that the fluid volumes in the stability region fully cover the area of the slit.

The pressure balancing portion of the present device includes communication between a point in the receptacle A, as well as a liquid inlet portion C at the lowermost end of the receptacle, and an air space B above a liquid supply portion and the liquid supply portion itself D, respectively. The balancing port is located such that the pressures at both ports in the collector equalize when the appropriate stable volume of fluid is present in the receptacle.

The device further includes a vacuum portion to draw ambient air or gas into the receptacle through the gas inlet. In one embodiment of the invention, the vacuum supply portion is a blower. The vacuum supply portion preferably provides enough vacuum such that ambient air or gas flows through the gas inlet slit at a sufficient rate to allow concentration of contaminants in real time. The rate may be anywhere from about 200 to about 600 liters per minute.

The liquid supply portion of the device includes liquids to be used as a sampling buffer and evaporation make-up to the receptacle. The liquid supply portion may further include a modifier used to convert a contaminant in the ambient air or gas sample being analyzed into a detectable substance.

It is preferred that the liquid supply portion includes a single-use removable cartridge that serves to supply liquid to the receptacle as well as to contain the sample after the run of the device is complete, and a removable multi-use non-buffered liquid bag that provides liquid to replenish what is lost to evaporation.

In another aspect of the present invention, the device includes an evaporative-makeup liquid supply portion to deliver liquid to the liquid supply portion when needed.

The device may further include any sort of detector, such as an ion chromatograph, for use in detecting substances in the sample or during sample acquisition.

The device may further include trigger means upstream of the gas inlet, such as a particle counter.

BRIEF DESCRIPTION OF THE DRAWINGS

FIG. 5 is a perspective view of an exemplary embodiment of a liquid supply portion in accordance with the present invention.

DETAILED DESCRIPTION OF THE INVENTION

Figure 1:
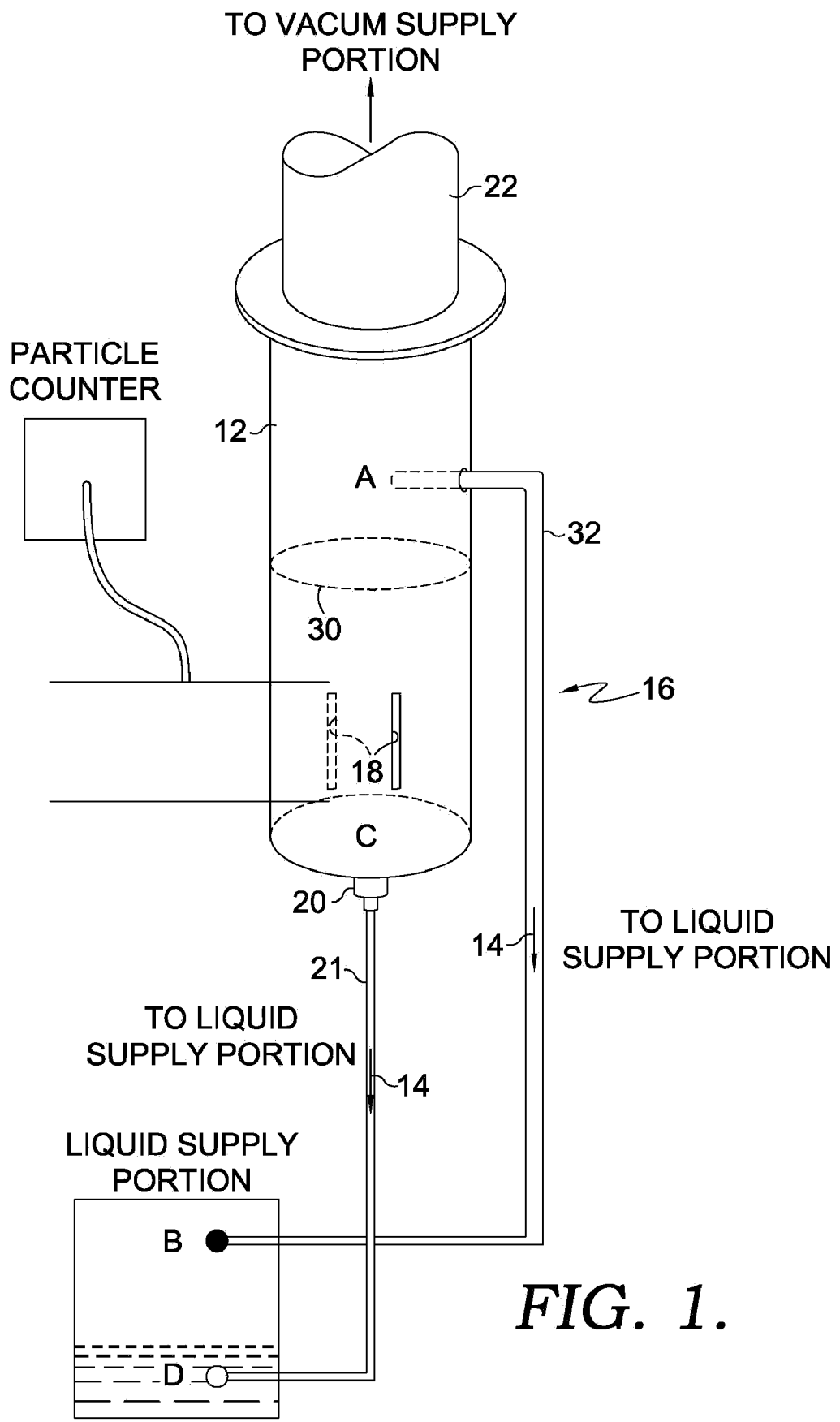
FIG. 1 is a schematic view of a receptacle 12 in accordance with the present invention.

Turning now to the drawings, wherein like numerals indicate like parts, the numeral 10 refers generally to a monitoring device constructed in accordance with the teachings of the present invention. The device comprises a receptacle 12, a liquid supply portion 14, and a pressure-balancing portion 16. Receptacle 12 includes gas inlet slits 18, a liquid transport 20, and a gas outlet 22. Though various embodiments of the present invention may be constructed, some of which are described below, these features of the device are common to the various embodiments and make up, as described below, the core of the invention.

In the embodiment of the present invention shown in FIG. 1, receptacle 12 is an upright, quickly removable cylindrical receptacle, preferably made of glass or clear acrylic plastic annealed to resist cracking during use. Receptacle 12 has a relatively thin cylindrical wall 24 having gas inlet slits 18 extending therethrough. As airflow is initiated through receptacle 12 via a vacuum supply portion 26, described below, a negative pressure is produced within receptacle 12. As a result, the pressure inside liquid supply portion 14 is greater than the pressure inside receptacle 12. This forces liquid from liquid supply portion 14 into receptacle 12 by way of supply line 21. As the liquid level in receptacle 12 rises, it begins to approach a stability point where the pressures at points 30 and 20 cause no more liquid to enter the receptacle (indicating the maximum stable liquid level allowed by receptacle 12). The intermingling of ambient air or gas from gas inlet 18 with liquid present on an interior surface of receptacle 12 results in the evaporation of the liquid in receptacle 12. Once enough liquid in receptacle 12 has evaporated during use of device 10, a significant pressure differential will again be created and liquid will move into receptacle 12 once more. Device 10 contains a liquid reservoir 44 connected to supply portion 14 via pump and valve manifold 36. A sensing means monitors the liquid level in supply 14 and automatically adds liquid from reservoir 44 when necessary to allow for continuous operation. After use of device 10 for collecting a sample, the liquid in receptacle 12, now containing compounds found in the ambient air or gas being sampled, is preferably returned to removable liquid supply portion 14 for storage until additional analysis is undertaken. Alternatively, liquid in receptacle 12 may, after use of device 10 for sampling, be transported directly to a portion of device 10 intended to undertake additional analysis of the sample, such as, for example, an ion chromatograph, a PCR portion, an immunoassay portion, a gas chromatograph, a spectrophotometer, or a combination thereof. In some embodiments of device 10, aliquots of sample may be removed from liquid supply portion 14 or receptacle 12 by action of device 10 in order to archive a portion of the sample for purposes of future testing or to directly analyze the portion. Accordingly, a withdrawing portion in communication with a liquid outlet of receptacle 12 may be utilized to withdraw a stream of liquid. In such a case, a chemical processing module in communication with the withdrawing portion may utilize an inlet to receive the stream of liquid from the withdrawing portion. The chemical processing module may be adapted to convert a contaminated sample in the liquid, on a real-time basis, to an analyte in detectable form indicative of the presence of a contaminant in the liquid. In one embodiment, an analytical portion in communication with the chemical processing module may analyze the liquid and determine the presence of a contaminant. Alternatively, an analytical portion in communication with the chemical processing module may analyze the liquid and determine a quantity of a contaminant.

Receptacle 12 includes a gas inlet slit 18 for introduction into receptacle 12 of a stream of air or other gas to be sampled. Gas inlet slit 18 is preferably off-tangential to the wall of receptacle 12 such that the stream of air or other gas to be sampled passes through the liquid in receptacle 12 as the gas enters receptacle 12, additionally causing the circulating liquid film to breakup, thereby increasing the contact area between the air and liquid. In one embodiment, air enters the receptacle 12 tangentially and causes fluid to spin, i.e., effects cyclonic spinning of the air or gas within the receptacle 12. Preferably, gas inlet slit 18 is sized, shaped, and positioned such that the slit is completely covered by the liquid within receptacle 12 when the fluid volume is within the stability region. This allows for a greater portion of the air or gas stream entering receptacle 12 to come in contact with the liquid therein. Because of this, a smaller blower or other vacuum supply portion 26 may be used, resulting in less power usage to effectively sample the same amount of air as a similarly constructed device having a gas inlet slit extending beyond the level of the liquid in receptacle 12. In the present device, wherein gas inlet slit 18 is covered by the liquid in receptacle 12, the smaller vacuum supply portion 26 requires less power than a larger vacuum supply portion, allowing the present device to be lighter and more portable than a comparable device requiring a larger vacuum supply portion. In some embodiments of device 10, receptacle 12 may be provided with a plurality of gas inlet slits or holes.

Receptacle 12 is adapted for easy cleaning, being readily removable from device 10. For example, receptacle 12 may be adapted to simply slide in and out of core module 42 (described below), with connections by connector lines 21 and 32 easily removed from one receptacle 12 and attached to another. This allows not only for convenient, fast cleaning of receptacle 12 by removing receptacle 12 from core module 42, but also allows for the simple replacement of receptacle 12 should such replacement be necessary. Replacement of receptacle 12 may be necessary if receptacle 12 is cracked or in some other way broken, or may be desired if an additional sample is to be tested immediately following a prior sample, without contamination of the samples between receptacles 12. Receptacle 12 can be replaced with a different receptacle that provides optimum performance for a different sampling protocol (i.e. receptacle 12 need not be exchanged for an identical replacement). In addition to simply sliding in and out of core module 42, receptacle 12 may be held firmly in place by blower module 46 (described below). Blower module 46 may be hinged such that it may be at least partially disengaged from core module 42, allowing receptacle 12 to be removed therefrom.

As noted above, receptacle 12 is preferably constructed from a clear, acrylic plastic adapted to withstand the conditions to which receptacle 12 is exposed during use of device 10. Alternatively, receptacle 12 may be constructed from borosilicate glass, or other suitable material. Depending on the particular use to which device 10 is to be put (i.e. the chemicals present in liquid supply portion 14, or the identity of the gases or other compounds to be monitored), the material from which receptacle 12 is constructed may be limited by chemical compatibility with other components of device 10 or the sample to be tested.

Liquid supply portion 14 of the present device may be any liquid reservoir suitable for holding the liquid to be supplied to receptacle 12 and accepting additional fluid as necessary without disrupting the fluid control in receptacle 12. Preferably, liquid supply portion 14 is a removable single-use cartridge (described more fully below and shown in FIG. 5) that contains an initial liquid charge, as well as accepts fluid from liquid reservoir 44 to provide on demand liquid to receptacle 12 during use of device 10. Liquid supply portion 14 may supply receptacle 12 with, for example, purified water, buffered solution, or any other liquid suitable for use with the present invention. In some instances, for example, in addition to a liquid, such as purified water provided in liquid supply portion 14, a modifier may be included to enable detection of certain contaminants transferred to the liquid from a contaminated air or gas stream being analyzed. For example, when monitoring a gas sample for the presence of certain metals, such as chromium, it may be necessary to utilize a basic solution (such as KOH) to stabilize a particular oxidation state of the metal. With chromium, KOH may be used to stabilize the +6 oxidation state of the metal, and to prevent reduction to chromium (III). The KOH may be provided by a line extending from a KOH source (not shown) to liquid supply portion 14, whereupon it mixes with the liquid in liquid supply portion 14, or, in an embodiment of the present invention wherein liquid supply portion 14 is a pre-filled single-use cartridge, the KOH or other modifier may be included with the liquid in the cartridge. Liquid supply portion 14 preferably also serves as the final sample container for device 10.

Pressure balancing portion 16 preferably includes a connector line 32 that communicates an area within receptacle 12 that is not contacted by the liquid in the receptacle with an air space within liquid supply portion 14. Thus, liquid supply portion 14 is effectively connected to receptacle 12 in two locations (i.e. via liquid inlet 20, connected to receptacle 12 and liquid supply portion 14 by connector line 21, and via pressure-balancing portion 16), and the difference between the locations of the connections between liquid supply portion 14 and receptacle 12, along with the amount of liquid in receptacle 12, creates a pressure balance that allows liquid to gradually flow from liquid supply portion 14 to receptacle 12 as liquid evaporates from receptacle 12.

Device 10 further includes a vacuum supply portion 26 to draw air or other gas to be analyzed through gas inlet slit 18 and into receptacle 12. In the embodiment of device 10 shown in FIG. 2, vacuum supply portion 26 is a blower positioned downstream of an outlet 22 of receptacle 12. When the blower is activated, air or other gas is pulled from the ambient environment into receptacle 12 through gas inlet slit 18. It is preferred that the air or other gas from the ambient environment is pulled into receptacle 12 at a sufficient rate such that contaminants in the ambient air or other gas are concentrated in the liquid in receptacle 12 in real-time. The required flow rate of air or other gas into receptacle 12 may vary depending on the specific application for which device 10 is used and the desired configuration of receptacle 12. In common situations sampling the ambient air, for example, air may be pulled into receptacle 12 at a rate of from about 200 to about 600 liters per minute. The rate of air flow through receptacle 12 may be measured by an air flow sensor (not shown) located anywhere within the air path through device 10, though preferably either downstream of vacuum supply portion 26 or between vacuum supply portion 26 and receptacle 12.

Figure 2:
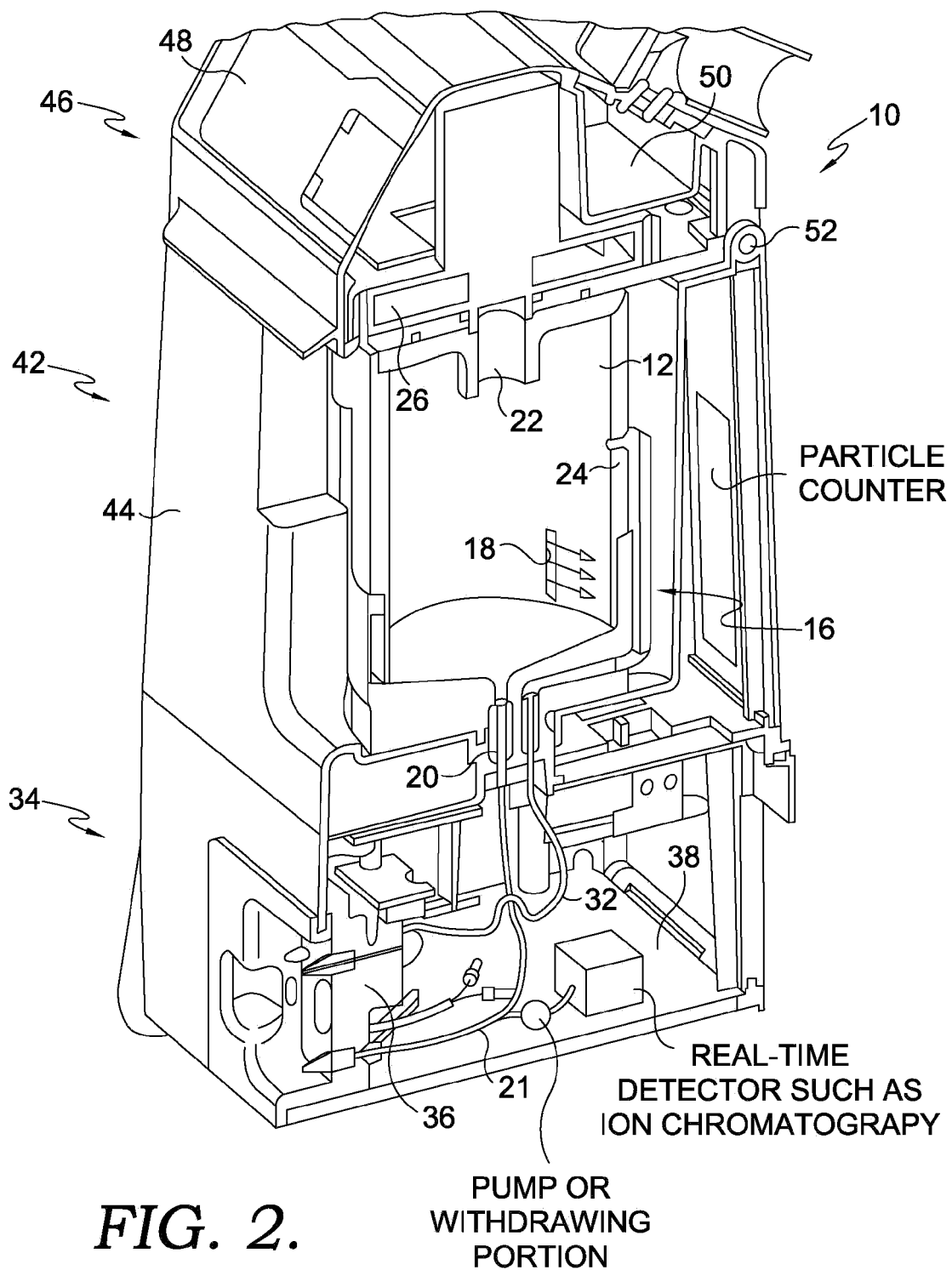
FIG. 2 is a schematic view of a device for continuous real-time collection of materials in ambient air in accordance with the present invention.

In the embodiment of the present invention shown in FIG. 2, device 10 includes three modules, a fluidics module, a core module, and a blower module. This embodiment of device 10 is adapted for use with a single-use removable cartridge as liquid supply portion 14.

As shown in FIG. 2, fluidics module 34 includes the lower approximately one-third of device 10. This module includes manifold 36, which provides the structure and capacity for the connections of various valves, pumps, lines, and the like, as well as sample cartridge/manifold interface and batteries (not shown) at 38. Manifold 36 enables control of all fluid-related functions of device 10, such as charging of liquid in liquid supply portion 14, control of liquid level during sampling, extraction of sample, and cleaning of the system. Preferably, device 10 utilizes only a single pump and valve configuration to achieve these functions. In one embodiment, manifold 36 may be utilized to pressurize air into the air space B of the liquid supply portion 14. In such an embodiment, fluid D within the liquid supply portion 14 may be forced out through connector line 21. As such, air may be introduced into the liquid supply portion 14 to achieve rapid startup of the device. Fluidics module 34 includes connector line 21 at the interface of connector line 21 and liquid supply portion 14, with connector line 21 extending into the core module for connection to liquid inlet 20. Liquid from liquid supply portion 14 moves into receptacle 12 by way of connector line 21. In addition, connector line 32 is positioned in fluidics module 34 such that it is in communication with an air space in liquid supply portion 14 and above a liquid level therein. Connector line 32 is part of the pressure-balancing system of device 10, as described above.

Figure 4:
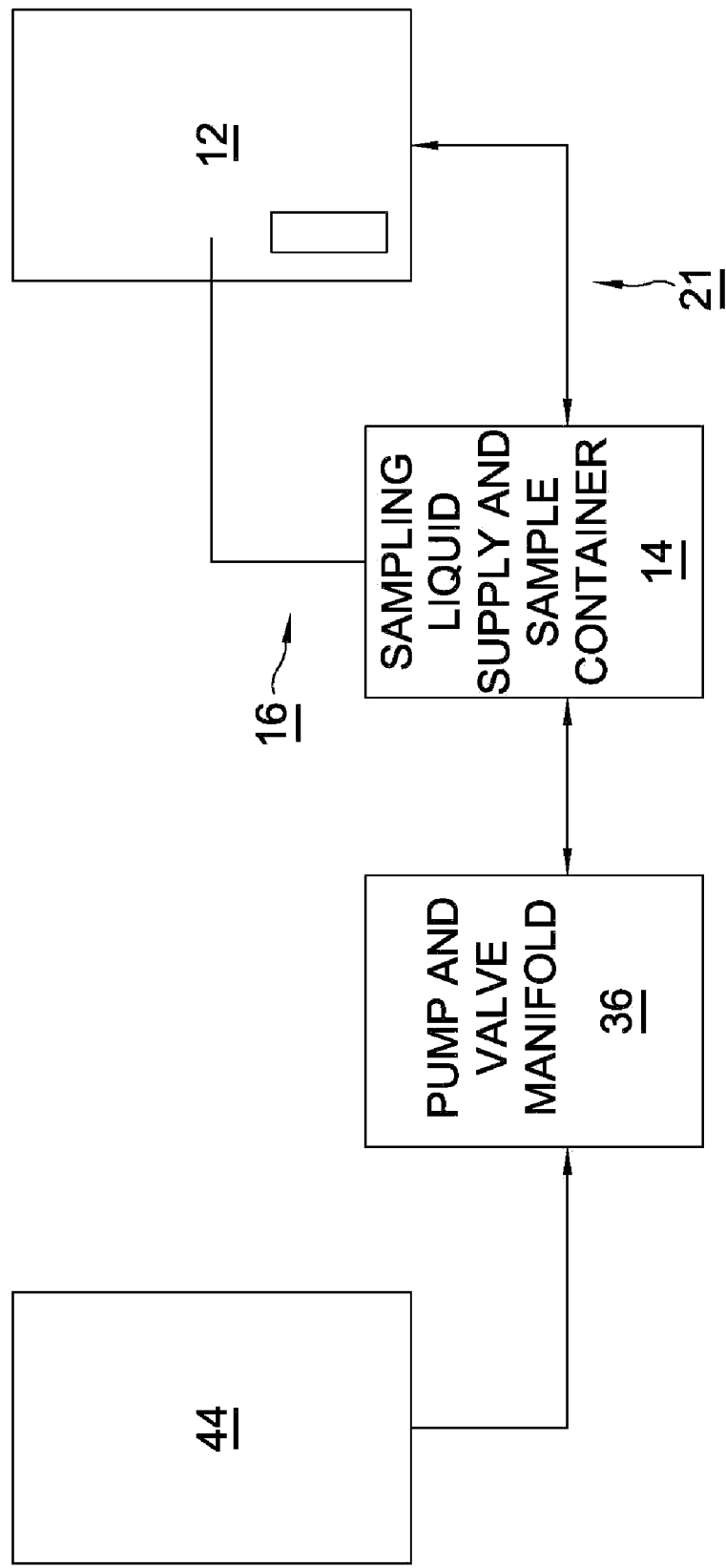
FIG. 4 is a schematic of a system constructed in accordance with the present invention.

As shown in FIG. 4, reservoir 44 is connected to liquid supply portion 14, which allows for long duration operation. Further, reservoir 44 could be replaced by continuous liquid supply means, such as a deionized water system, enabling continuous operation.

As shown in FIG. 2, core module 42 includes the middle approximately one-third of device 10. Core module 42 includes receptacle 12, which is adapted to be readily removable from device 10 for easy cleaning of receptacle 12, and evaporative make-up liquid supply portion 44. Receptacle 12 may be designed to be readily removed from device 10 in any suitable manner. In the embodiments shown, for example, blower module 46 includes a hinge 52 that allows blower module 46 to at least partially disengage from core module 42, thereby allowing for easy removal of receptacle 12 and liquid supply portion 44. Receptacle 12 has a gas inlet slit 18 in a wall thereof, as described more fully above. Evaporative make-up liquid supply portion 44 preferably contains a volume of non-buffered liquid similar to that included in liquid supply portion 14 (in this embodiment, a removable single-use cartridge; not shown). Should the liquid supply in liquid supply portion 14 be exhausted prior to the end of a particular sampling run, device 10 can draw liquid into receptacle 12 from evaporative make-up liquid supply portion 44. Evaporative make-up liquid supply portion 44 may be a compartment or container area built into the structure of device 10, or may be any other suitable holder of a liquid supply that is attached or attachable to device 10. In one embodiment of the present invention, evaporative make-up liquid supply portion 44 includes a bag constructed from a rugged polymer material, such that the bag will not break when transported in the field, and is designed to be quickly attached to and removed from device 10 in order to provide a evaporative make-up fluid supply when necessary.

Figure 3:
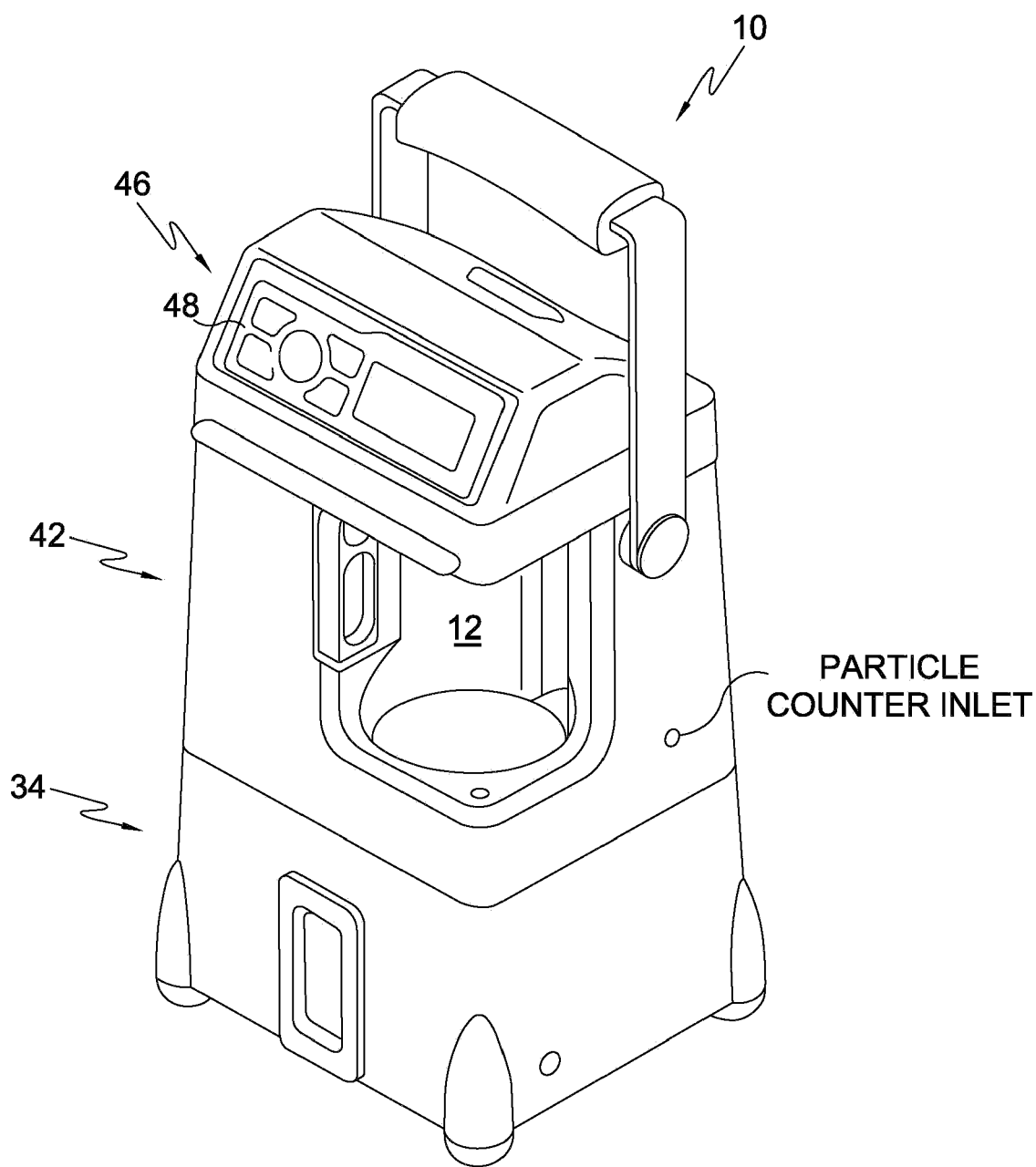
FIG. 3 is a perspective view of a device for continuous real-time monitoring of ambient air in accordance with the present invention.

As can be seen in FIG. 2, blower module 46 includes the upper approximately one-third of device 10. Blower module 46 includes vacuum supply portion 26 (a blower in the embodiment of device 10 shown in FIG. 3). Vacuum supply portion 26 draws ambient air or other gas to be sampled into receptacle 12 through gas inlet slit 18, and vents gas from receptacle 12 through outlet 22. Blower module 46 may also include a user interface 48 (as best shown in FIG. 3) and a muffler 50. User interface 48 may be of any suitable type of user interface known in the art, and preferably allows a user to program or configure collection cycles, or to calibrate device 10 when using additional attachments on the inlet or exhaust. User interface 48 may also provide data logging and may provide the user with certain system-specific information such as flow rate, cycle length, and the like, and may also include system alarms to alert the user if device 10 is outside of pre-determined operating parameters. Muffler 50 may include any of a number of mufflers known in the art and suitable for use with device 10. The presence of muffler 50 serves to reduce the amount of noise generated by device 10 during use.

In addition to the above, device 10 may be provided with a particle detection portion (such as a particle counter) upstream of receptacle 12, such that the device may monitor the number of particles entering the system and finalize a collection cycle at or after a predetermined particle count. Further, the particle counter may be active even when device 10 is not in use, counting particles in the ambient environment such that device 10 is triggered to begin a sampling cycle upon detection of a threshold level of particles in the air. In the latter instance, it is preferred that the particle detection portion operate at a reduced rate in order to conserve battery power.

FIG. 5 depicts an exemplary embodiment of removable liquid supply portion 14 of the present invention. In the embodiment shown, liquid supply portion 14 has three valves 56 through which a liquid may be introduced into or removed from liquid supply portion 14. In an alternative embodiment, an additional valve 56 may be placed at the position of indentation 54 shown in FIG. 5. The valves 56 of liquid supply portion 14 may be used to communicate liquid to or from liquid supply portion 14 for any of a variety of purposes required by use of device 10. For example, a valve 56 may be used in communication with a storage portion (not shown), such as a vial or test tube. In such an embodiment, an aliquot of a liquid sample from receptacle 12 maybe transferred to the storage portion for storage until said aliquot is needed. Further, a valve 56 may be placed in communication with a detection system such that, periodically, liquid is removed from liquid supply portion 14 and transferred to said detection system for sample analysis. Also, an additional liquid supply portion (not shown) may be used in association with a valve 56 such that liquid from the additional liquid supply may be communicated to receptacle 12. This additional liquid may include a buffer, reactant, or any other liquid solution desired to be combined with the liquid present in receptacle 12.

Each of the various components of device 10 may be constructed from a variety of materials, as will be readily apparent to those of skill in the art upon reading this disclosure. Materials may be selected, for example, according to weight, durability, insulating qualities, and the like. Portions of device 10 contacting liquid from liquid supply portion 14, the ambient gas or air sample, liquid containing the sample therein, or a modifier compound, such as KOH, should be chosen for chemical compatibility with the compounds they are to contact during use of device 10, including periods of cleaning such as that done during decontamination using dilute bleach or alcohol.

The specific embodiments of the present invention described above are provided by way of example only, and are not meant to limit the subject matter of the present invention. Various alterations and modifications to the above will be apparent to those of skill in the art upon reading this disclosure.

The invention claimed is:

1. A device for capturing material into liquids to monitor ambient air or other gas under observation, said device comprising:
   a receptacle having a generally cylindrical wall presenting an inside surface, said wall having at least one gas inlet slit therein;
   a liquid supply portion communicating with said receptacle for supplying a liquid thereto; and
   a pressure balancing portion communicating with said receptacle, and
   communicating with said liquid supply portion whereby to equalize the pressure in the receptacle and the liquid supply portion such that the liquid in the receptacle is maintained at a desired operating level, said liquid substantially covering said at least one gas inlet slit.

2. The device according to claim 1 wherein said at least one gas inlet slit is positioned off-tangential to said cylindrical wall.

3. The device according to claim 1 further comprising:
   an evaporative make-up liquid supply portion having an evaporative make-up liquid therein, said evaporative make-up liquid supply portion in communication with said liquid supply portion,
   wherein said evaporative make-up liquid is automatically added to said liquid supply portion as needed without disrupting pressure balance volume control.

4. The device according to claim 1 wherein said receptacle further includes an upper end and a lower end, further comprising:
   a vacuum supply portion communicating with an upper end of said receptacle for continuously flowing air or other gas under observation into said receptacle through said at least one gas inlet slit to cause contact of said air or gas and said liquid and effect cyclonic spinning of the air or gas within said receptacle.

5. The device according to claim 4 wherein said vacuum supply portion provides a sufficient vacuum such that air or gas flows through said gas inlet slit at a rate sufficient to enable concentration of contaminants in said liquid to occur in real time.

6. The device according to claim 4 wherein said liquid supply portion supplies said liquid at a flow rate of up to about twenty milliliters per minute at startup and less than about twenty milliliters per minute during operation, and said vacuum supply portion flows air or gas into said receptacle at a rate of from about 200 to about 600 liters per minute.

7. The device according to claim 4 wherein air is forced into said liquid supply portion in order to achieve rapid startup of said device.

8. The device according to claim 1 wherein said liquid supply portion further includes a modifier to said liquid for conditioning said liquid to provide, upon contact with a contaminant, on a real-time basis, a detectable substance indicative of the presence of said contaminant in said liquid.

9. The device according to claim 8 further comprising a detector in communication with said receptacle for receiving said conditioned liquid, said detector analyzing said liquid in real time to determine the presence of a contaminant therein.

10. The device according to claim 1 further comprising a detector in communication with said receptacle for receiving said liquid, said detector analyzing said liquid in real time to determine the presence of a contaminant therein.

11. The device according to claim 1 further comprising:
a withdrawing portion in communication with a liquid outlet of said receptacle for withdrawing a stream of said liquid therefrom; and
a chemical processing module in communication with said withdrawing portion and having an inlet for receiving said stream of said liquid from said withdrawing portion, said chemical processing module adapted to convert a contaminated sample in said liquid, on a real-time basis, to an analyte in detectable form indicative of the presence of a contaminant in said liquid.

12. The device according to claim 11 further comprising an analytical portion in communication with said chemical processing module for analyzing said liquid and determining the presence of the contaminant therein.

13. The device according to claim 11 further comprising an analytical portion in communication with said chemical processing module for analyzing said liquid and determining a quantity of the contaminant therein.

14. The device of either claims 12 or 13 wherein said analytical portion is selected from the group consisting of an ion chromatograph, a PCR portion, an immunoassay portion, a gas chromatograph, a spectrophotometer, and combinations thereof.

15. The device according to claim 1 wherein said liquid supply portion is removable by hand and comprises a disposable single-use pre-filled cartridge.

16. The device according to claim 1 wherein said receptacle is removable by hand.

17. The device according to claim 1 further comprising a particle detection portion in communication with said receptacle, said particle detection portion adapted to detect particles emerging from said receptacle and to disengage said device after detecting a predetermined number of particles.

18. The device according to claim 1 further comprising a particle detection portion in communication with the ambient air, said particle detection portion adapted to detect particles in the ambient air and to engage said device after detecting a predetermined number of particles.

19. The device of claim 1 further comprising an evaporative make-up liquid supply portion in communication with said liquid supply portion for delivering liquid to said liquid supply portion.

20. A device for capturing material into liquids to monitor ambient air or other gas under observation, said device comprising:
a receptacle having a generally cylindrical wall presenting an inside surface, said wall having at least one gas inlet slit therein;
a liquid supply portion in communication with said receptacle for supplying liquid thereto;
an evaporative make-up liquid supply portion in communication with said liquid supply portion for supplying liquid thereto; and
a pressure balancing portion communicating with said receptacle, and communicating with said liquid supply portion, whereby to equalize the pressure in the receptacle and the liquid supply portion such that the liquid in the receptacle is maintained at a desired operating level.

* * * * *